(12) United States Patent
Cheng et al.

(10) Patent No.: US 9,737,512 B2
(45) Date of Patent: Aug. 22, 2017

(54) METHODS AND COMPOSITIONS FOR TREATING CHRONIC PAIN

(71) Applicants: Xiaodong Cheng, Houston, TX (US); Fang Mei, Houston, TX (US); Annemieke Kavelaars, Houston, TX (US); Cobi J. Heijnen, Houston, TX (US)

(72) Inventors: Xiaodong Cheng, Houston, TX (US); Fang Mei, Houston, TX (US); Annemieke Kavelaars, Houston, TX (US); Cobi J. Heijnen, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/066,416

(22) Filed: Mar. 10, 2016

(65) Prior Publication Data
US 2016/0263088 A1    Sep. 15, 2016

Related U.S. Application Data

(60) Provisional application No. 62/131,821, filed on Mar. 11, 2015.

(51) Int. Cl.
*A61K 31/42*     (2006.01)
*A61K 31/422*    (2006.01)
*A61K 31/41*     (2006.01)
*A61K 31/275*    (2006.01)
*A61K 31/33*     (2006.01)

(52) U.S. Cl.
CPC .......... *A61K 31/422* (2013.01); *A61K 31/275* (2013.01); *A61K 31/42* (2013.01); *A61K 31/33* (2013.01)

(58) Field of Classification Search
CPC ...... A61K 31/42; A61K 31/422; A61K 31/33; A61K 31/41
USPC ................................ 514/277, 359, 375, 378
See application file for complete search history.

(56) References Cited

U.S. PATENT DOCUMENTS

| 2006/0100166 | A1  | 5/2006 | De Koning et al. ............ 514/45 |
| 2007/0060548 | A1* | 3/2007 | Levine ................. A61K 31/685 514/78 |
| 2009/0049622 | A1  | 2/2009 | Matsunaga et al. .............. 8/426 |
| 2009/0169540 | A1  | 7/2009 | Lezoualc'h et al. ....... 424/130.1 |
| 2010/0113379 | A1  | 5/2010 | Rubinsztein et al. .......... 514/46 |

(Continued)

FOREIGN PATENT DOCUMENTS

WO    WO/2009/033284    3/2009

OTHER PUBLICATIONS

Wang et al, "Balancing GRK2 and EPAC1 levels prevents and relieves chronic pain," J. Clinical Investigations (2013), vol. 123 (No. 12), pp. 5023-5034.*

(Continued)

*Primary Examiner* — Kamal Saeed
*Assistant Examiner* — Janet L Coppins
(74) *Attorney, Agent, or Firm* — Norton Rose Fulbright US LLP

(57) ABSTRACT

Certain embodiments are directed to methods of treating pain, e.g., chronic or neuropathic pain, comprising administering an effective amount of an EPAC inhibitor.

12 Claims, 7 Drawing Sheets

(56) References Cited

U.S. PATENT DOCUMENTS

| | | | |
|---|---|---|---|
| 2011/0060029 A1 | 3/2011 | Iwatsubo et al. | ............ 514/44 A |
| 2011/0251182 A1 | 10/2011 | Sun et al. | ..................... 514/218 |

OTHER PUBLICATIONS

Zhu et al, "Biochemical and Pharmacological Characterizations of ESI-09 Based EPAC Inhibitors," Scientific Reports (2015), vol. 5, pp. 1-8.*
Breckler et al., *Cellular signaling*, 2011, 23:1257-66.
Chan et al. (2009) *Cell Microbiol* 11(4):629-644.
Chan et al. (2010) *Front Microbiol* 1:139.
Cheung et al. (2012)*Am J Physiol Heart Circ Physiol* 303(11):H1374-H1383.
Cullere et al. (2005) *Blood* 105(5):1950-1955.
De Rooij et al. (1998) *Nature* 396: 474-477.
Eijkelkamp et al., *The Journal of neuroscience*, 2010, 30:12806-15.
Eijkelkamp, et al., *The Journal of neuroscience*, 2010, 30:2138-49.
Fukuhara et al. (2005) *Mol Cell Biol* 25(1):136-146.
Gong et al. (2012) *PLoS Negl Trop Dis* 6(6):e1699.
Huston et al. (2008) *Proc Natl Acad Sci USA* 105(35):12791-1279647.
International Preliminary Report on Patentability in International Application No. PCT/US2013/025319 dated Aug. 12, 2014.
International Search Report and Written Opinion in International Application No. PCT/US2013/025319 dated Apr. 15, 2013.
Kawasaki et al. (1998) *Science* 282: 2275-2279.
Kooistra et al. (2005) *FEBS Lett* 579(22):4966-4972.
Martinez and Cossart (2004) *J Cell Sci* 117(Pt 21):5097-5106.
Martinez et al. (2005) *Cell* 123(6):1013-1023.
McDonough & Rodriguez (2012) *Nature Rev Microbiol* 10:27-38.
Pannekoek et al. (2011) *Cell Signal* 23(12):2056-2064.
Rampersad et al. (2010) *J Biol Chem* 285(44):33614-33622.
Schmidt (2013) *Pharmacol Rev* 65(2):670-709.
Schnoor et al. (2011) *J Exp Med* 208(8):1721-1735.
Shirshev (2011) *Biochemistry (Mosc)* 76:981-998.
Spindler et al. (2011) *Am J Pathol* 179(4):1905-1916.
Tsalkova, et al., "Isoform-specific antagonists of exchange proteins directly activated by cAMP" PNAS. 109(45):18613-8, 2012.
Walker and Ismail (2008) *Nat Rev Microbiol* 6(5):375-386.
Wang et al., *The Journal of clinical investigation*, 2013, 123:5023-34.
Wang, et al., *Pain*, 2011, 152:1649-58.
Yeager et al (2009) *Infect Immun* 77:2530-2543.

* cited by examiner

| NO | Structure | HPLC | HRMS | IC$_{50}$ (μM) |
|---|---|---|---|---|
| ESI-09 | 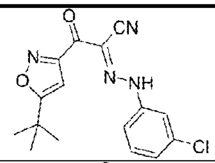 | $t_R$ = 21.72 min 99.6% | 331.0969 | 4.4 |
| HJC0683 | 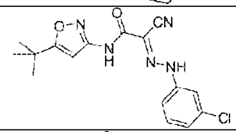 | $t_R$ = 20.97 min 96.7% | 346.1074 | >300 |
| HJC0692 | 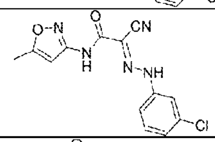 | $t_R$ = 18.55 min 98.5% | 304.0606 | >300 |
| HJC0693 | 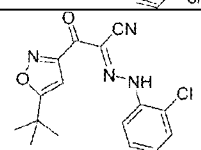 | $t_R$ = 22.77 min 96.6% | 331.0969 | 34 |
| HJC0694 | 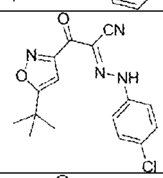 | $t_R$ = 21.74 min 98.1% | 331.0963 | 20 |
| HJC0695 | 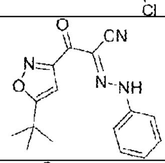 | $t_R$ = 20.50 min 99.4% | 297.1355 | 73 |
| HJC0696 | 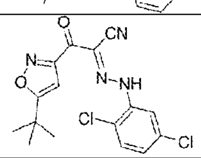 | $t_R$ = 23.69 min 97.1% | 365.0576 | 7.7 |
| HJC0712 | 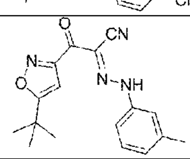 | $t_R$ = 21.29 min 99.0% | 311.1514 | 22.7 |
| HJC0720 | 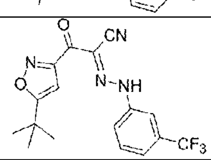 | $t_R$ = 21.80 min 96.0% | 365.1230 | 15.6 |
| HJC0721 | 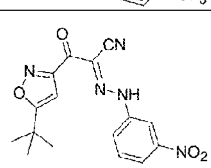 | $t_R$ = 20.33 min 96.4% | 342.1207 | 30 |

FIG. 5

| | | | | |
|---|---|---|---|---|
| HJC0724 | (5-tert-butylisoxazol-3-yl-CO-C(CN)=N-NH-(4-methylphenyl)) | $t_R$ = 21.36 min 98.6% | 311.1515 | 57 |
| HJC0726 | (5-tert-butylisoxazol-3-yl-CO-C(CN)=N-NH-(3,5-dichlorophenyl)) | $t_R$ = 23.20 min 99.0% | 365.0563 | 1.0 |
| HJC0742 | (5-tert-butylisoxazol-3-yl-CO-C(CN)=N-NH-(4-bromophenyl)) | $t_R$ = 22.01 min 98.9% | 375.0455 | 16 |
| HJC0743 | (5-tert-butylisoxazol-3-yl-CO-C(CN)=N-NH-(3-bromophenyl)) | $t_R$ = 21.93 min 98.3% | 375.0456 | 11 |
| HJC0744 | (5-tert-butylisoxazol-3-yl-CO-C(CN)=N-NH-(2,5-dimethylphenyl)) | $t_R$ = 23.01 min 98.6% | 325.1664 | >300 |
| HJC0745 | (5-tert-butylisoxazol-3-yl-CO-C(CN)=N-NH-quinolinyl) | $t_R$ = 16.09 min 97.8% | 348.1458 | 77 |
| HJC0750 | (5-tert-butylisoxazol-3-yl-CO-C(CN)=N-NH-(2,3-dichlorophenyl)) | $t_R$ = 23.74 min 97.5% | 365.0568 | 25 |
| HJC0751 | (5-tert-butylisoxazol-3-yl-CO-C(CN)=N-NH-(3-ethynylphenyl)) | $t_R$ = 20.83 min 96.2% | 321.1350 | 72 |
| HJC0752 | (5-tert-butylisoxazol-3-yl-CO-C(CN)=N-NH-(3-CO$_2$Et-phenyl)) | $t_R$ = 21.53 min 98.8% | 369.1558 | 85 |
| HJC0753 | (5-tert-butylisoxazol-3-yl-CO-C(CN)=N-NH-(3-cyanophenyl)) | $t_R$ = 19.87 min 99.3% | 322.1303 | 72 |

FIG. 5 cont.

| | | | | |
|---|---|---|---|---|
| HJC0754 |  | $t_R$ = 19.80 min 98.2% | 339.1459 | >300 |
| HJC0755 |  | $t_R$ = 22.69 min 95.7% | 325.1666 | 270 |
| HJC0756 |  | $t_R$ = 17.86 min 99.6% | 327.1457 | >300 |
| HJC0757 |  | $t_R$ = 22.47 min 99.6% | 337.1664 | 27 |
| HJC0758 |  | $t_R$ = 22.96 min 96.4% | 433.1098 | 6.8 |
| HJC0759 |  | $t_R$ = 20.02 min 96.5% | 375.0858 | >300 |
| HJC0760 |  | $t_R$ = 18.89 min 99.0% | 347.0909 | >300 |
| HJC0768 |  | $t_R$ = 19.18 min 98.4% | 289.0492 | 106 |
| HJC0770 |  | $t_R$ = 20.79 min 98.4% | 323.0103 | 18 |

METHODS AND COMPOSITIONS FOR TREATING CHRONIC PAIN

PRIORITY

This application claims priority to U.S. Provisional Patent Application Ser. No. 62/131,821 filed Mar. 11, 2015, which is incorporated herein by reference in its entirety.

STATEMENT REGARDING FEDERALLY FUNDED RESEARCH

This invention was made with government support under GM066170 and NS074999 awarded by the National Institutes of Health. The government has certain rights in the invention.

BACKGROUND

Pain can exerted in different forms and normally serves as a warning signal to protect the body from harmful stimuli or promote healing after injury. However, under pathological conditions, pain is sensed without harmful stimuli and can persist. Chronic pain is a long lasting pain that persists longer than the temporal course of natural healing of the underlying causative injury or disease. It serves no beneficial or protective function. Chronic pain is a major debilitating disorder that affects one-third of the general population during their adult life-span.

Cancer pain is one of the most common types of chronic pain and demonstrates nociceptive components due to tumor growth and neuropathic components due to tumor induced nerve damage. It can further involve structural damage, nerve entrapment and damage, inflammatory processes that lead to the disruption of normal tissue metabolism, the production of inflammatory prostaglandins and cytokines, and tissue damage.

The cyclic AMP signaling pathway is the first pathway identified in regulating pain sensitivity. Recent study suggests that the cAMP receptor (the classic cAMP-dependent protein kinase (PKA)) is more closely related in regulation of acute pain while cAMP sensors (exchange proteins directly activated by cAMP (EPAC1 and EPAC2)) contribute to development of chronic pain. To date, the main analgesics employed for treatment of chronic pain are opiates and non-steroidal anti-inflammatory drugs (NSAIDS). Both classes of drugs can produce severe side-effects—NSAIDS can cause gastric ulceration and renal damage and opiates can cause nausea, constipation, confusion and dependency problems. Opioids fail to produce pain relief in all individuals suffering chronic pain, even at high doses, and development of analgesic resistance to opioids complicates their utility for long-term therapy. In particular, cancer pain treatment requires the use of unacceptably high levels of opiates bringing with it side-effects and at least 20% of treated patients still have uncontrolled pain.

Accordingly, there is a critical medical need to identify new pharmaceutically active compounds that interfere with key steps of the chronic pain process and particularly for the treatment and/or prevention of chronic nociceptive pain and/or symptoms of chronic nociceptive pain.

SUMMARY

Chronic pain is a major health problem associated with multiple conditions such as cancer, chemotherapy, surgery, arthritis, fibromyalgia, and diabetes. Currently, there are limited treatment options. Chronic pain is defined as pain that extends beyond the expected period of healing, in certain instance chronic pain can have lasted longer than three to six months. In contrast, acute pain is pain that lasts less than 30 days. Neuropathic pain is a localized sensation of unpleasant discomfort caused by damage or disease that affects the somatosensory system. Neuropathic pain may be associated with abnormal sensations called dysesthesia and pain from normally non-painful stimuli (allodynia). Neuropathic pain may have continuous and/or episodic components. The episodic components can resemble stabbings or electric shocks. Common qualities of neuropathic pain include burning or coldness, "pins and needles" sensations, numbness and itching.

Certain embodiments are directed to methods of treating pain, e.g., chronic or neuropathic pain, comprising administering an effective amount of an EPAC inhibitor. In certain aspects the EPAC inhibitor is ESI-09. In certain aspects the EPAC inhibitor is administered at a dose of between 0.001 mg/kg and 1 mg/kg body weight, preferably between about 1 and 100 μg/kg body weight, most preferably between 1 and 10 μg/kg body weight, including all values and ranges there between. In certain aspects a subject can be administered a dose of EPAC inhibitor of at least, about, or at most 5, 10, 20, 30, 40, 50, 60, 70, 80, 90, 100, 150, 200, 250, 300, 350, or 500 mg, including all values and ranges there between, can be used. In a further aspect the dose of EPAC inhibitor is administered in one dose or in multiple doses over 0.5, 1, 2, 3, 4, 5, 6, 7, 8, 9, or 10 minutes, hours, or days. An EPAC inhibitor can be formulated as a tablet, a capsule, a concentrate, a powder, a beverage, an injectable solution, or the like. In certain aspects an EPAC-1 inhibitor is administered orally.

The present invention is directed to a medicament for the prevention and/or treatment of chronic pain and/or symptoms of chronic pain and methods for prevention and/or treatment of chronic pain and/or symptoms of chronic pain in an individual.

The terms "inhibiting," "reducing," or "preventing," or any variation of these terms, when used in the claims and/or the specification includes any measurable decrease or complete inhibition to achieve a desired result.

As used herein, an "inhibitor" as described herein, for example, can inhibit directly or indirectly the activity of a protein. The term "EPAC inhibitor" refers to a compound that decreases the activity of EPAC in a cell. EPAC inhibitors include EPAC1-specific inhibitors, EPAC2-specific inhibitors, and/or pan-EPAC inhibitors (which inhibit both EPAC1 and EPAC2).

As used herein, "treatment" is an approach for obtaining beneficial or desired clinical results. For purposes of this invention, beneficial or desired clinical results include, but are not limited to, one or more of the following: improvement or alleviation of any aspect of chronic pain and/or symptom of chronic pain. For purposes of this invention, beneficial or desired clinical results include, but are not limited to, one or more of the following: including lessening severity, alleviation of pain and/or a symptom associated with chronic pain.

An "effective amount" of drug, compound, or pharmaceutical composition is an amount sufficient to effect beneficial or desired results including clinical results such as alleviation or reduction in pain sensation. An effective amount can be administered in one or more administrations. For purposes of this invention, an effective amount of drug, compound, or pharmaceutical composition is an amount sufficient to treat, ameliorate, reduce the intensity of and/or prevent chronic pain or symptom associated with chronic pain. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" or "subject" is a vertebrate, preferably a mammal, more preferably a human. Mammals include, but are not limited to, farm animals (such as cows), sport animals, pets (such as cats, dogs and horses), and laboratory animals (e.g., primates, mice and rats).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

In FIG. 1B, *$p<0.05$,  $p<0.01$ for WT versus HO, #$p<0.05$, ##$P<0.01$ for WT versus HE, +$p<0.05$, ++$p<0.01$ for HE versus HO. In FIG. 1D, $p<0.01$ and ##$p<0.01$ are ESI-09 50 mg/kg and ESI-09 20 mg/kg compared to the Vehicle treated mice.

DESCRIPTION

Figure 1:
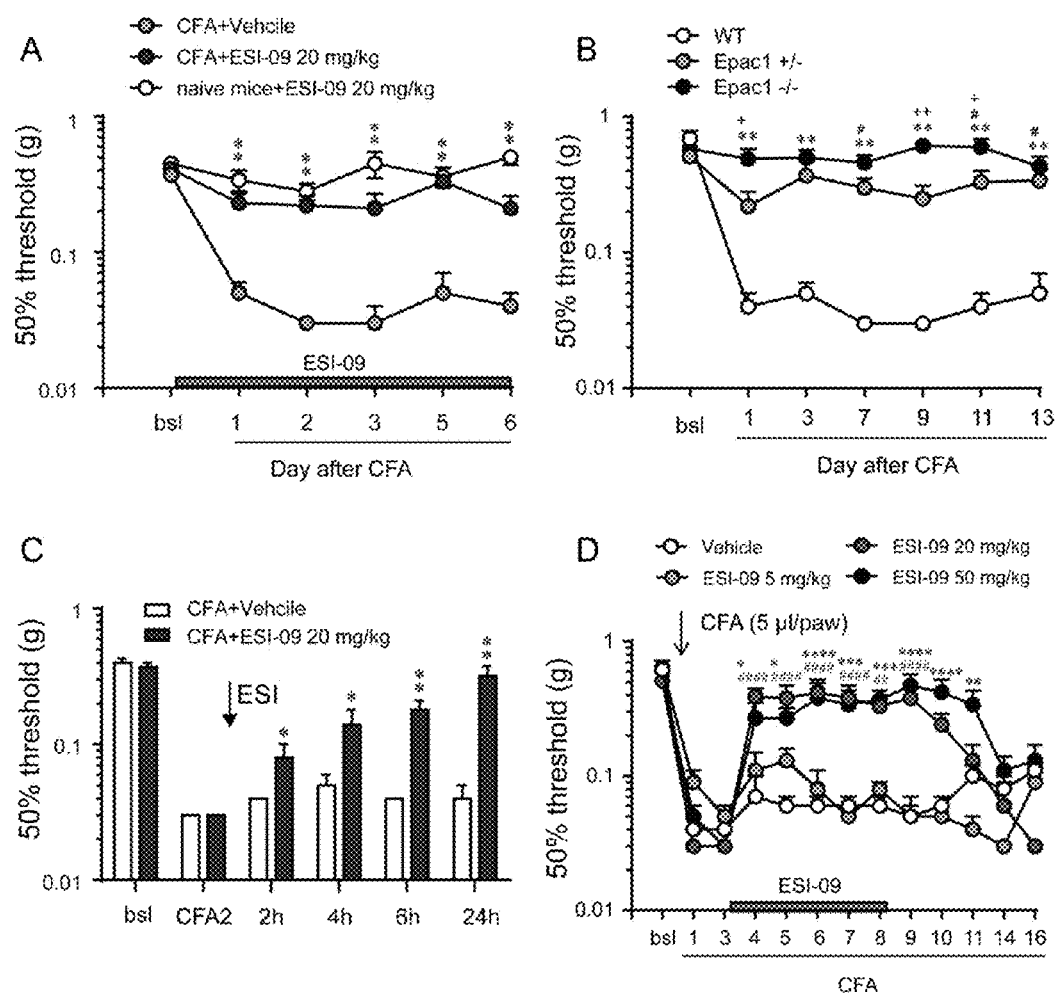
FIG. 1. Effect of ESI-09 in CFA-induced inflammatory mechanical allodynia. (A) Mice (n=4/group) received 5 µl CFA intraplantarly in the hind paws and were treated with vehicle or ESI-09 20 mg/kg (n=4) daily by oral gavage for 6 days starting immediately after CFA injection. Mechanical allodynia was quantified with von Frey Hairs using the up and down method at 24 hours after ESI treatment. (B) CFA-induced mechanical allodynia in WT, heterozygous, and homozygous Epac1-knockout mice. The sensitivity to mechanical stimulation was followed over time in wild-type (WT, n=3), Epac1$^{+/-}$ (HE, n=6) and Epac1$^{-/-}$ (HO, n=5) mice after intraplantar injection of 5 µl CFA. (C) Early time points of ESI-09 (20 mg/kg) administration started on the 3$^{rd}$ day after CFA, when mechanical allodynia is fully developed (n=4/group). (D) Dose-response curve for the effect of ESI-09 (5, 20, or 50 mg/kg). Treatment was started on the 3$^{rd}$ day after CFA administration (n=4/group) (E) Mechanical allodynia was measured in WT mice with 6 days treatments of ESI-09 20 (n=3) and 50 mg/kg (n=4) to control for a potential effect on baseline mechanical sensitivity. Data are expressed as 50% withdrawal threshold in grams calculated as described in the methods section and represent mean±SEM. Repeated measures one-way analysis of variance (ANOVA) showed a significant genotype effect.

The discovery of "exchange proteins directly activated by cAMP" (Epacs) has led to a paradigm change for the understanding of signaling mediated by cAMP (de Rooij et al., *Nature*, 1998, 396:474-77; Kawasaki et al., *Science*, 1998, 282:2275-79). It is now clear that cAMP not only signals through protein kinase A (PKA) and cAMP-activated ion channels, but also via Epacs. Epac-mediated cAMP signaling regulates exocytosis, tumor cell migration, cell proliferation, cytokine secretion, integrin-mediated cell adhesion, and cadherin-mediated cell junction formation in multiple cell types (Breckler et al., *Cellular signaling*, 2011, 23:1257-66).

Epacs are guanine nucleotide exchange factors (GEF) catalyzing the exchange of GDP for GTP for the Ras-like GTPases Rap1 and Rap2, resulting in activation of these small GTP-binding proteins (de Rooij et al., *Nature*, 1998, 396:474-77; Kawasaki et al., *Science*, 1998, 282:2275-79). Activated Rap signal to e.g. Akt (Mei et al., *The Journal of biological chemistry*, 2002 277:11497-504), PLC-ε (Schmidt et al., *Nature cell biology*, 2001, 3:1020-24), PKC, and MAPKs (Breckler et al., *Cellular signaling*, 2011, 23:1257-66).

The two Epac isoforms, Epac1 and Epac2 are multidomain proteins harboring a regulatory region at the N-terminus including a Disheveled/Egl-10/pleckstrin (DEP) domain and a cAMP-sensing cyclic nucleotide-binding domain. The catalytic region at the C-terminus contains a Ras exchange motif (REM), a Ras association domain (RA), and a Rap1-binding CDC25-homology (CDC25-HD) domain (de Rooij et al., *The Journal of biological chemistry*, 2000, 275:20829-836). Subcellular localization of Epac1 is dynamic and spatio-temporally regulated. Agonist stimulation induces rapid translocation of cytosolic Epac1 to the plasma membrane where it binds to phosphatidic acid via its DEP-domain and activates a local Rap1 pool (Ponsioen et al., *Molecular and cellular biology*, 2009, 29:2521-31; Vliem et al., *Chembiochem: a European journal of chemical biology*, 2008, 9:2052-54; Consonni et al., *Proc. Acad. Natl. Sci. USA.*, 2012, 109:3814-19).

The serine-threonine kinase G protein-coupled receptor kinase 2 (GRK2) desensitizes G protein-coupled receptor (GPCR) and regulates activity of downstream signaling molecules including extracellular signal-regulated protein kinases 1 and 2 (Erk1/2), protein kinase B (Akt), p38 mitogen-activated protein kinases, and phosphoinositide-dependent kinase-1 (PDK-1) (Kleibeuker et al., *The European journal of neuroscience*, 2007, 25:1696-1704; Penela et al., *British journal of pharmacology*, 2010, 160:821-32). The balance of GRK2/Epac1 plays a role in chronic pain (Wang et al., *The Journal of clinical investigation*, 2013, 123:5023-34; Eijkelkamp et al., *The Journal of neuroscience*, 2010, 30:12806-15). Chronic inflammatory pain is associated with a decrease in GRK2 levels in pain sensing neurons, and that either increasing GRK2 protein levels or reducing Epac1 levels prevents chronic pain (Wang et al., *The Journal of clinical investigation*, 2013, 123:5023-34). Similarly, mice heterozygous for deletion of GRK2 in nociceptors develop a prolonged pain response to cAMP-inducing agents like PGE2 and epinephrine, as well as to the specific Epac1 agonist 8-pCPT-2'-O-Me-cAMP (8-pCPT), but not in response to the PKA selective agonist 6-Bnz-cAMP (Eijkelkamp et al., The Journal of neuroscience, 2010, 30:12806-15; Eijkelkamp, et al., *The Journal of neuroscience*, 2010, 30:2138-49; Wang, et al., Pain, 2011, 152:1649-58).

I. EPAC INHIBITORS

Inhibitors of EPAC are known. For instance, the inventors have developed a sensitive and robust high throughput screening (HTS) assay for the purpose of identifying EPAC specific inhibitors (Tsalkova et al. (2012) *PLOS ONE* 7(1): e30441). Using this EPAC HTS assay, the inventors have successfully identified several isoform-specific EPAC inhibitors that are capable of blocking biochemical and cellular cAMP-induced EPAC activation (Tsalkova et al. (2012) *Proc. Acad. Natl. Sci. USA.* 109:18613-18; Almahariq et al., (2013) *Molecular Pharmacology*, 83:122-128). In addition, the inventors have synthesized and characterized a number of chemical analogs of these EPAC specific inhibitors (ESI) (Chen et al. (2012) *Bioorganic & Medicinal Chemistry Letters.* 22:4038-43; Chen et al. (2014) *J. Med. Chem.*, 57:3651-65). EPAC specific inhibitors will not only provide a powerful pharmacological tool for dissecting the physiological functions of EPAC and for further elucidating the molecular mechanism of cAMP signaling, but also have important impacts on designing potential therapeutics targeting EPAC in diseases where cAMP signaling and EPAC proteins have been implicated. The structure and function of various EPAC inhibitors is described in PCT application serial number PCT/US2013/025319 entitled "Modulators of Exchange Proteins Directly Activated by cAMP (EPACs)," which is incorporated herein by reference.

Certain embodiments are directed to the use of Exchange Protein Activated by cAMP (EPAC) modulating compound having a formula of:

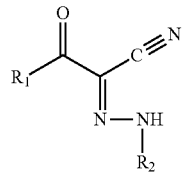

Formula I where, in certain aspects, $R_1$ and $R_2$ are independently substituted or unsubstituted cycloalkyl, substituted or unsubstituted heterocycle, substituted or unsubstituted aryl, or substituted or unsubstituted heteroaryl.

In certain embodiments $R_1$ is an unsubstituted or substituted isoxazole. In certain aspects the isoxazole is attached via the 3 position. In certain aspects the substituted isoxazole is a 4-substituted isoxazole, a 5-substituted isoxazole, or a 4,5-substituted isoxazole. In a particular aspect the substituted isoxazole is a 5-substituted isoxazole. In certain aspects the substituent is independently a cycloalkyl or a branched or unbranched $C_1$ to $C_{10}$ alkyl. In certain aspects the alkyl is a methyl, ethyl, n-propyl, iso-propyl, n-butyl, sec-butyl, iso-butyl, tert-butyl, neo-pentyl, n-pentyl, or isopenyl. In certain embodiments the isoxazole is a 5-methyl or 5 tert-butyl isoxazole. In a further aspect $R_1$ can be a substituted to unsubstituted phenyl.

In certain embodiments $R_2$ is a monocyclic or polycyclic, substituted or unsubstituted aryl or heteroaryl. In certain aspects $R_2$ is a substituted phenyl or N-containing heteroaryl. In a further aspect the substituted phenyl is a 2; 3; 4; 5; 6; 2,3; 2,4; 2,5; 2,6; 3,4; 3,5; 3,6; 4,5; 4,6; or 5,6 substituted phenyl. In still further aspects the phenyl comprises one or more substituent selected from bromo, fluoro, chloro, iodo, $C_1$-$C_4$ alkyl, hydroxy, nitro, fluoromethyl, difluoromethyl, trifluoromethyl, nitrile, $C_1$-$C_4$ alkynyl, acetyl, $C_1$-$C_4$ hydroxyalkyl, $C_1$-$C_4$ alkoxy, or carboxyl group. In certain aspects $R_2$ is a substituted or unsubstituted benzopyridine or a substituted or unsubstituted indane. In certain aspects $R_2$ is a 3-chlorophenyl; 2-chlorophenyl;

4-chlorophenyl; phenyl; 3,6-dichlorophenyl; 3-methylphenyl, 3-trifluoromethylphenyl; 3-nitrophenyl; 4-methylphenyl, 3,5-dichlorophenyl; 4-bromophenyl; 3-bromophenyl; 3,6-dimethylphenyl; benzopyridine; 2,3-dichlorophenyl; 3-ethynyl; benzoic acid ethyl ester; 3-benzonitrile; 3-acetylphenyl; 2,3-methylphenyl; 3-ethoxyphenyl; indane; 3,5-ditrifluoromethylphenyl; 6-chloro-benzoic acid; or 3-chloro, 4-hydroxyphenyl.

In certain aspects a compound of Formula I is selected from N-(5-tert-Butyl-isoxazol-3-yl)-2-[(3-chlorophenyl)-hydrazono]-2-cyanoacetamide (HJC0683); 24(3-Chlorophenyl)-hydrazono]-2-cyano-N-(5-methyl-isoxazol-3-yl)acetamide (HJC0692); 3-(5-tert-Butyl-isoxazol-3-yl)-2-[(3-chlorophenyl)-hydrazono]-3-oxo-propionitrile (HJC0680, ESI-09); 3-(5-tert-Butyl-isoxazol-3-yl)-2-[(2-chlorophenyl)-hydrazono]-3-oxo-propionitrile (HJC0693); 3-(5-tert-Butyl-isoxazol-3-yl)-2-[(4-chlorophenyl)-hydrazono]-3-oxo-propionitrile (HJC0694); 3-(5-tert-Butyl-isoxazol-3-yl)-3-oxo-2-(phenyl-hydrazono)-propionitrile (HJC0695); 3-(5-tert-Butyl-isoxazol-3-yl)-2-[(2,5-dichlorophenyl)-hydrazono]-3-oxo-propionitrile (HJC0696); 3-(5-tert-Butyl-isoxazol-3-yl)-3-oxo-2-(m-tolyl-hydrazono)propionitrile (HJC0712); 3-(5-tert-Butyl-isoxazol-3-yl)-3-oxo-2-[(3-trifluoromethyl-phenyl)-hydrazono]propionitrile (HJC0720); 3-(5-tert-Butyl-isoxazol-3-yl)-2-[(3-nitrophenyl)-hydrazono]-3-oxo-propionitrile (HJC0721); 3-(5-tert-Butyl-isoxazol-3-yl)-3-oxo-2-(p-tolyl-hydrazono)propionitrile (HJC0724); 3-(5-tert-Butyl-isoxazol-3-yl)-2-[(3,5-dichlorophenyl)-hydrazono]-3-oxo-propionitrile (HJC0726); 2-[(4-Bromophenyl)-hydrazono]-3-(5-tert-butyl-isoxazol-3-yl)-3-oxo-propionitrile (HJC0742); 24(3-Bromophenyl)-hydrazono]-3-(5-tert-butyl-isoxazol-3-yl)-3-oxo-propionitrile (HJC0743); 3-(5-tert-Butyl-isoxazol-3-yl)-2-[(2,5-dimethylphenyl)-hydrazono]-3-oxo-propionitrile (HJC0744); 3-(5-tert-Butyl-isoxazol-3-yl)-3-oxo-2-(quinolin-6-yl-hydrazono)propionitrile (HJC0745); 3-(5-tert-Butyl-isoxazol-3-yl)-2-[(2,3-dichlorophenyl)-hydrazono]-3-oxo-propionitrile (HJC0750); 3-(5-tert-Butyl-isoxazol-3-yl)-24(3-ethynyl-phenyl)-hydrazono]-3-oxo-propionitrile (HJC0751); 3-{N-[2-(5-tert-Butyl-isoxazol-3-yl)-1-cyano-2-oxo-ethylidene]-hydrazino}benzoic acid ethyl ester (HJC0752); 3-{N-[2-(5-tert-Butyl-isoxazol-3-yl)-1-cyano-2-oxo-ethylidene]-hydrazino}benzonitrile (HJC0753); 2-[(3-Acetyl-phenyl)-hydrazono]-3-(5-tert-butyl-isoxazol-3-yl)-3-oxo-propionitrile (HJC0754); 3-(5-tert-Butyl-isoxazol-3-yl)-2-[(2,3-dimethylphenyl)-hydrazono]-3-oxo-propionitrile (HJC0755); 3-(5-tert-Butyl-isoxazol-3-yl)-2-[(3-hydroxymethylphenyl)-hydrazono]-3-oxo-propionitrile (HJC0756); 3-(5-tert-Butyl-isoxazol-3-yl)-2-(indan-5-yl-hydrazono)-3-oxo-propionitrile (HJC0757); 2-[(3,5-Bis-trifluoromethyl-phenyl)-hydrazono]-3-(5-tert-butyl-isoxazol-3-yl)-3-oxo-propionitrile (HJC0758); 2-{N42-(5-tert-Butyl-isoxazol-3-yl)-1-cyano-2-oxo-ethylidene]-hydrazino}-6-chloro-benzoic acid (HJC075 9); 3-(5-tert-Butyl-isoxazol-3-yl)-2-[(3-chloro-4-hydroxy-phenyl)-hydrazono]-3-oxo-propionitrile (HJC0760); 2-[(3-Chloro-phenyl)-hydrazono]-3-(5-methyl-isoxazol-3-yl)-3-oxo-propionitrile (HJC0768); or 2-[(3,5-Dichlorophenyl)-hydrazono]-3-(5-methyl-isoxazol-3-yl)-3-oxo-propionitrile (HJC0770).

ESI-09 is one example an EPAC inhibitor. ESI-09 is a non-cyclic nucleotide. ESI-09 is a potent, specific inhibitor of EPAC (exchange protein directly activated by cAMP). ESI-09 inhibits EPAC1 and EPAC2 with $IC_{50}$ values of 3.2 and 1.4 µM, respectively, with no activity against PKA at 25 µM. In pancreatic cell lines, the compound blocks phosphorylation of Akt and insulin secretion. ESI-09 inhibits migration of pancreatic cancer cell lines. In vivo application of ESI-09 with a daily dose of 10 mg/kg IP treatment or 50 mg/kg oral gavage has been shown to recapitulate the EPAC1 knockout phenotypes of protecting mice from lethal rickettsioses (Gong et al (2013) Proc. Acad. Natl. Sci. USA. 110:19615-20) and of compromising ovalbumin-induced oral tolerance (Almahariq et al., (2015) Biochem. J. 465: 295-303).

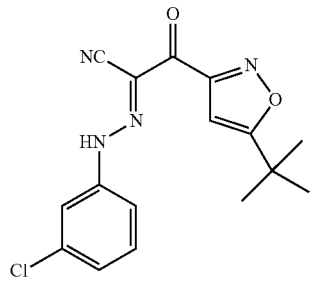

ESI-09

II. TREATING CHRONIC OR NEUROPATHIC PAIN

Embodiments are directed to methods and/or a medicament for the prevention and/or treatment of chronic or neuropathic pain and/or symptoms of chronic or neuropathic pain in an individual. In certain aspects, the methods are directed to providing or administering an EPAC inhibitor for the prevention and/or treatment of chronic pain and/or symptoms of chronic pain. In certain aspects the EPAC inhibitor is prepared for administration to a subject experiencing chronic or neuropathic pain.

A further aspect is directed to the use of an EPAC inhibitor for the manufacture of a medicament for ameliorating, controlling, reducing incidence of, or delaying the development or progression of chronic pain and/or symptoms of chronic pain.

Certain aspects are directed to methods of preventing and/or treating chronic pain and/or symptoms of chronic pain in an individual, comprising administering to the individual of an effective amount of an EPAC inhibitor.

In certain aspects the individual or subject is a mammal, for example a companion animal such as a horse, cat or dog or a farm animal such as a sheep, cow or pig. In a further aspect the mammal is a human.

In certain embodiments the medicament and/or EPAC inhibitor is prepared for oral, sublingual, buccal, topical, rectal, inhalation, transdermal, subcutaneous, intravenous, intraarterial, intrathecal, intramuscular, intraosseous, intradermal, intraperitoneal, transmucosal, intra-articular, periarticular, local, epidural, or epicutaneous administration.

According to certain embodiments the medicament is prepared for administration prior to and/or during and/or after the development of chronic pain or administration of a therapy (e.g., chemotherapy, surgery, etc.). In certain aspects the EPAC inhibitor is administered centrally, spinally, or intrathecally.

In certain aspects the chronic pain is chronic nociceptive pain, chronic neuropathic pain, chronic inflammatory pain, chemotherapy-induced pain, fibromyalgia, breakthrough pain and/or persistent pain. The chronic pain may comprise one or more of hyperalgesia, allodynia, central sensitization, peripheral sensitization, disinhibition, and spontaneous pain.

In certain aspects the chronic pain is cancer pain, preferably cancer pain arising from malignancy or from cancer. The cancer can be one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukemia, primary or secondary bone cancer, tumors that metastasize to the bone, tumors infiltrating the nerve and hollow viscus, tumors near neural structures. Further preferably the cancer pain comprises visceral pain, such as visceral pain that arises from pancreatic cancer and/or metastases in the abdomen. Further preferably the cancer pain comprises somatic pain, preferably somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

In certain aspects the cancer associated neuropathic pain is chemotherapy-induced neuropathic pain associated with chemotherapy-induced peripheral neuropathy (CIPN). CIPN is a frequent, dose-dependent complication of anticancer drugs including platinums, taxanes, epothilones, and vinca alkaloids. CIPN presents clinically as deficits in sensory, motor, and sometimes autonomic function. Sensory disturbances range from a mild tingling sensation to spontaneous burning pain and hypersensitivity to stimuli. Symptoms may occur at any time during the course of chemotherapy or even after termination.

In a further aspect the EPAC inhibitor is administered separately, sequentially or simultaneously (co-administered or co-formulated) in combination with one or more further pharmacologically active compounds or agents (i.e., secondary agents). In certain aspects, secondary agent can include agents useful for treating chronic pain. In one aspect the additional agent(s) is/are selected from one or more of:

(i) an opioid analgesic, e.g. morphine, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(ii) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398, or a pharmaceutically acceptable salt thereof;

(iii) a barbiturate sedative, e.g. amobarbital, aprobarbital, butabarbital, butabital, mephobarbital, metharbital, methohexital, pentobarbital, phenobartital, secobarbital, talbutal, theamylal or thiopental or a pharmaceutically acceptable salt thereof;

(iv) a sedative, e.g. glutethimide, meprobamate, methaqualone, dichloralphenazone chlordiazepoxide, clorazepate, diazepam, flurazepam, lorazepam, oxazepam, temazepam, triazolam, diphenhydramine, pyrilamine, promethazine, chlorpheniramine, chlorcyclizine or a pharmaceutically acceptable salt thereof;

(v) a skeletal muscle relaxant, e.g. baclofen, carisoprodol, chlorzoxazone, cyclobenzaprine, methocarbamol or orphrenadine or a pharmaceutically acceptable salt thereof; or (vi) other drugs such as dextromethorphan ((+)-3-hydroxy-N-methylmorphinan), dextrorphan ((+)-3-hydroxy-N-methylmorphinan), ketamine, memantine, pyrroloquinoline quinone, cis-4-(phosphonomethyl)-2-piperidinecarboxylic acid, doxazosin, tamsulosin, clonidine, 4-amino-6,7-dimethoxy-2-(5-methanesulfonamido-1,2,3,4-tetrahydroisoquinol-2-yl)-5-(2-pyridyl)quinazoline, carbamazepine, valproate, (aR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3 S)-2-[(1R)-1-[3,5-bis(trifluoromethyl)phenyl]ethoxy-3-(4-fluorophenyl)-4-morpholinyl] methyl]-1,2-dihydro-3H-1,2,4-triazol-3-one (MK-869), lanepitant, dapitant, 3-[[2-methoxy-5-(trifluoromethoxy) phenyl]methylamino]-2-phenyl-piperidine (2S,3S), oxybutin, tolterodine, propiverine, tropsium chloride, darifenacin, paracetamol, droperidol, resiniferatoxin, capsazepine, propranolol, mexiletine, dexamethasone, sildenafil, vardenafil, taladafil, gabapentin, pregabalin, desipramine, imipramine, amytriptiline, nortriptiline, amitriptyline (Elavil), trazodone (Desyrel), imipramine (Tofranil), phenyloin (Dilantin) or carbamazepine (Tegretol).

In further embodiments the secondary agent can be a therapeutic agent, such as an anti-cancer agent (e.g., a chemotherapeutic) or anti-diabetic agent.

Certain aspects are directed to providing a pharmaceutical composition for the prevention and/or treatment of chronic pain and/or symptoms of chronic pain or for ameliorating, controlling, reducing incidence of, or delaying the development or progression of chronic pain and/or symptoms of chronic pain in an individual, comprising an EPAC inhibitor and a pharmaceutically acceptable carrier and/or an excipient.

In one embodiment, "prepared for" herein means the medicament is in the form of a dosage unit or the like suitably packaged and/or marked for use in treating chronic pain.

"Reducing incidence" of chronic pain and/or a symptom associated with chronic pain means any of reducing severity (which can include reducing need for and/or amount of (e.g., exposure to) other drugs and/or therapies generally used for these conditions), duration, and/or frequency.

"Ameliorating" chronic pain and/or a symptom associated with chronic pain means a lessening or improvement of one or more symptoms of chronic pain and/or symptoms associated with chronic pain as compared to not administering an EPAC inhibitor. "Ameliorating" also includes shortening or reduction in duration of a symptom.

"Palliating" chronic pain and/or a symptom associated with chronic pain means lessening the extent of one or more undesirable clinical manifestations of chronic pain in an individual or population of individuals treated with an EPAC inhibitor in accordance with the invention.

As used therein, "delaying" the development of chronic pain means to defer, hinder, slow, retard, stabilize, and/or postpone progression of chronic pain and/or a symptom associated with chronic pain. This delay can be of varying lengths of time, depending on the history of the disease and/or individuals being treated. As is evident to one skilled in the art, a sufficient or significant delay can, in effect, encompass prevention, in that the individual does not develop chronic pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

III. CHEMICAL DEFINITIONS

Various chemical definitions related to EPAC modulating compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer. In certain aspects, one, both, or the predominant enantiomer forms or isomers are all covered.

As used herein, the term "nitro" means —$NO_2$; the term "halo" or "halogen" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear (i.e. unbranched) or branched carbon chain of 1, 2, 3, 4, 5, 6, 7, 8, 9, or 10 carbons, which may be fully saturated, mono-unsaturated, or polyunsaturated. An unsaturated alkyl group includes those having one or more carbon-carbon double bonds (alkenyl) and those having one or more carbon-carbon triple bonds (alkynyl). The groups, —$CH_3$ (Me, methyl), —$CH_2CH_3$ (Et, ethyl), —$CH_2CH_2CH_3$ (n-Pr, n-propyl), —$CH(CH_3)_2$ (iso-Pr, iso-propyl), —$CH_2CH_2CH_2CH_3$ (n-Bu, n-butyl), —$CH(CH_3)CH_2CH_3$ (sec-butyl), —$CH_2CH(CH_3)_2$ (iso-butyl), —$C(CH_3)_3$(tert-butyl), —$CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, S, and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, and —$CH_2Si(CH_3)_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule. Examples of cycloalkyl groups include cyclopropyl, cyclobutyl, cyclopentyl, cyclohexyl, and cycloheptyl groups. Examples of heterocyclic groups include indole, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, and the like.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 4-azaindole, 5-azaindole, 6-azaindole, 7-azaindole, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkyl sulfonyl, aryl sulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Examples of optional substituents include, but are not limited to: —OH, oxo (=O), —Cl, —F, —Br, $O_{-4}$alkyl, phenyl, benzyl, —$NH_2$, —$NH(C_{1-4}alkyl)$, —$N(C_{1-4}alkyl)_2$, —$NO_2$, —$S(C_{1-4}alkyl)$, —$SO_2(C_{1-4}alkyl)$, —$CO_2(C_{1-4}alkyl)$, and —$O(C_{1-4}alkyl)$.

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means oxygen that is double bonded to a carbon atom.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base, such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the three dimensional configuration of those atoms differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

IV. PHARMACEUTICAL FORMULATIONS AND ADMINISTRATION

In certain embodiments, the invention also provides compositions comprising one or more EPAC inhibitors with one or more of the following: a pharmaceutically acceptable diluent; a carrier; a solubilizer; an emulsifier; a preservative; and/or an adjuvant. Such compositions may contain an effective amount of at least one EPAC inhibitor. Thus, the use of one or more EPAC inhibitor as provided herein for the preparation of a medicament is also included. Such compositions can be used in the treatment of a variety of EPAC associated diseases or conditions such as chronic pain.

An EPAC inhibitor may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The form depends upon the mode of administration and the particular disease and/or tissue targeted. The compositions may also include pharmaceutically acceptable vehicles, carriers, or adjuvants, well known in the art.

Acceptable formulation components for pharmaceutical preparations are nontoxic to recipients at the dosages and concentrations employed. In addition to the EPAC inhibitors, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to an organ or a tumor is also contemplated by the present invention. When administering the compositions by injection, the administration may be by continuous infusion or by single or multiple boluses. For parenteral administration, the EPAC inhibitors may be administered in a pyrogen-free, parenterally acceptable aqueous solution comprising the desired EPAC inhibitors in a pharmaceutically acceptable vehicle. A particularly suitable vehicle for parenteral injection is sterile distilled water in which one or more EPAC inhibitors are formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

For the compounds of the present invention, alone or as part of a pharmaceutical composition, such doses are between about 0.001, 0.01, to 0.1 mg/kg and 0.05, 0.5, to 1 mg/kg body weight, preferably between about 1 and 100 µg/kg body weight, most preferably between 1 and 10 µg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

In some methods of the invention, an EPAC inhibitor is administered to a subject having chronic pain. In additional embodiments, an EPAC inhibitor can be administered directly, endoscopically, intrathecally, intratracheally, intravenously, intralesionally, intramuscularly, intraperitoneally, regionally, percutaneously, topically, intrarterially, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating chronic pain may further include administering to the subject an anti-inflammatory, which may be administered more than one time.

V. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Effect of ESI-09 on CFA-Induced Mechanical Allodynia and Thermal Hyperalgesia.

To determine whether the Epac inhibitor ESI-09 can be used to treat inflammatory pain, the CFA model was used. CFA was administered intraplantarly and mice were treated with ESI-09 20 mg/kg daily by oral gavage for 6 days starting immediately after injection of CFA. Mechanical allodynia was examined using the von Frey test. The data in FIG. 1A demonstrate that ESI-09 20 mg/kg strongly inhibited CFA-induced mechanical allodynia. Administration of ESI-09 to control mice did not have any effect on mechanical sensitivity.

ESI-09 Acts as an Inhibitor of Both Epac1 and Epac2.

Epac1 contributes to chronic inflammatory pain. To further establish the contribution of Epac1 to CFA-induced mechanical allodynia Epac1+/− and Epac1−/− mice was used. Epac1−/− mice did not develop detectable mechanical allodynia in response to intraplantar injection with CFA (FIG. 1C). A small, but statistically significant decrease in the threshold for withdrawal in Epac1+/− mice treated with CFA was observed, but mechanical allodynia in Epac1+/− mice was markedly reduced as compared to WT mice (FIG. 1C). Baseline mechanical sensitivity did not differ between WT, Epac1+/− and Epac1−/− mice. Overall these data indicate Epac1 is required for development of mechanical allodynia in the CFA model of chronic inflammatory pain and that treatment with the Epac inhibitor ESI-09 inhibits mechanical allodynia in this model.

The Treatment of ESI-09 could be Delayed Until the Mechanical Allodynia Induced by CFA is Fully Developed.

ESI-09 20 mg/kg was administered orally three days after CFA. Partial inhibition was observed at 2 hours after administration of ESI-09 (20 mg/kg), was fully developed at 6 hours and was maintained until at least 24 h after administration (FIG. 1C). The effect of ESI-09 was dose-dependent (FIG. 1D). Both 20 mg/kg and 50 mg/kg ESI-09 significantly reduced mechanical allodynia (FIG. 1A). At the lowest dose tested (5 mg/kg) the inventors did not observe an effect of ESI-09 on mechanical allodynia. The beneficial effect of ESI-09 was detectable until at least 24 hours after the last dose. No effect of daily oral administration of 50 mg/kg ESI-09 on mechanical sensitivity in saline treated control mice was observed (FIG. 1D).

Figure 2:
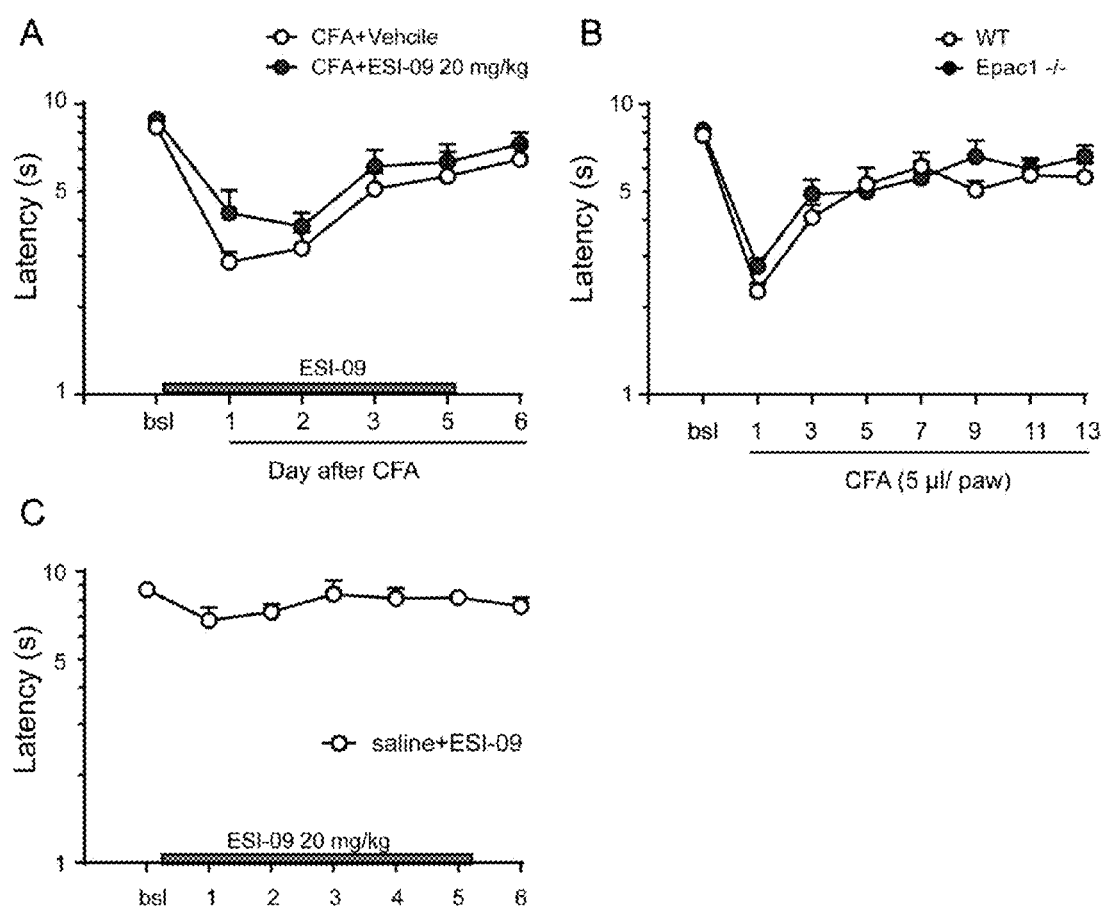
FIG. 2. Effect of ESI-09 on CFA-induced heat hyperalgesia. (A) Mice (n=4/group) received 5 µl CFA intraplantarly in the hind paws and were treated with vehicle or ESI-09 20 mg/kg (n=4) daily by oral gavage for 6 days starting after CFA injection. Heat hyperalgesia was determined using the Hargreaves test and is expressed as heat-withdrawal latency in seconds. (B) CFA-induced heat hyperalgesia in WT and Epac1-/- mice. (C) Heat sensitivity of saline treated mice with 20 mg/kg ESI-09. Data represent mean±SEM (n=4 per group).
Figure 3:
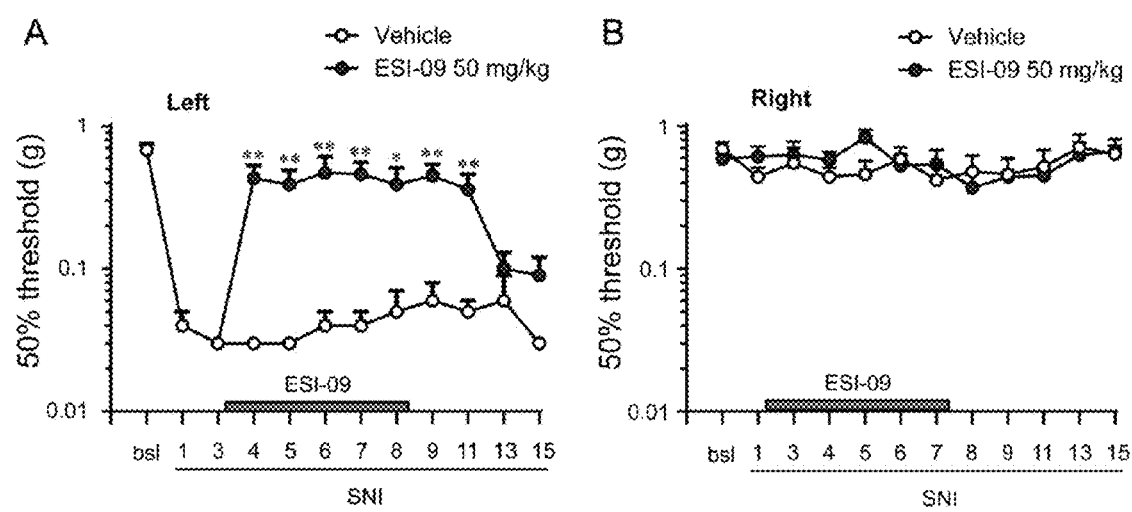
FIG. 3. Effect of ESI-09 on Spared nerve injury (SNI)-induced mechanical allodynia. Spared nerve injury was performed on WT mice and mice were treated daily with ESI-09 (50 mg/kg) or vehicle by oral gavage for 6 days starting on the 3$^{rd}$ day after SNI. Mechanical allodynia was monitored in (A) ipsi- and (B) contralateral paw using von Frey hairs and the up and down method at 24 hours after ESI-treatment (n=7 per group). Data are expressed as 50% paw withdrawal thresholds calculated as described in the methods section and represent mean±SEM. n=7/group. *$p<0.05$, **$p<0.01$ vs. vehicle group.

Intraplantar administration of CFA also induces significant heat hyperalgesia (FIG. 2A). However, no effect of ESI-09 (20 mg/kg) on heat hyperalgesia was detected (FIG. 2A). Consistently, CFA-induced heat hyperalgesia was not different between WT and Epac1−/− mice. ESI-09 did not affect heat sensitivity of naïve animals and heat sensitivity of Epac1−/− mice was similar to that of WT mice.

Effect of ESI-09 or Epac1 Deletion on Inflammatory Activity in the CFA Model. Effect of ESI-09 in a Model of Neuropathic Pain.

Figure 4:
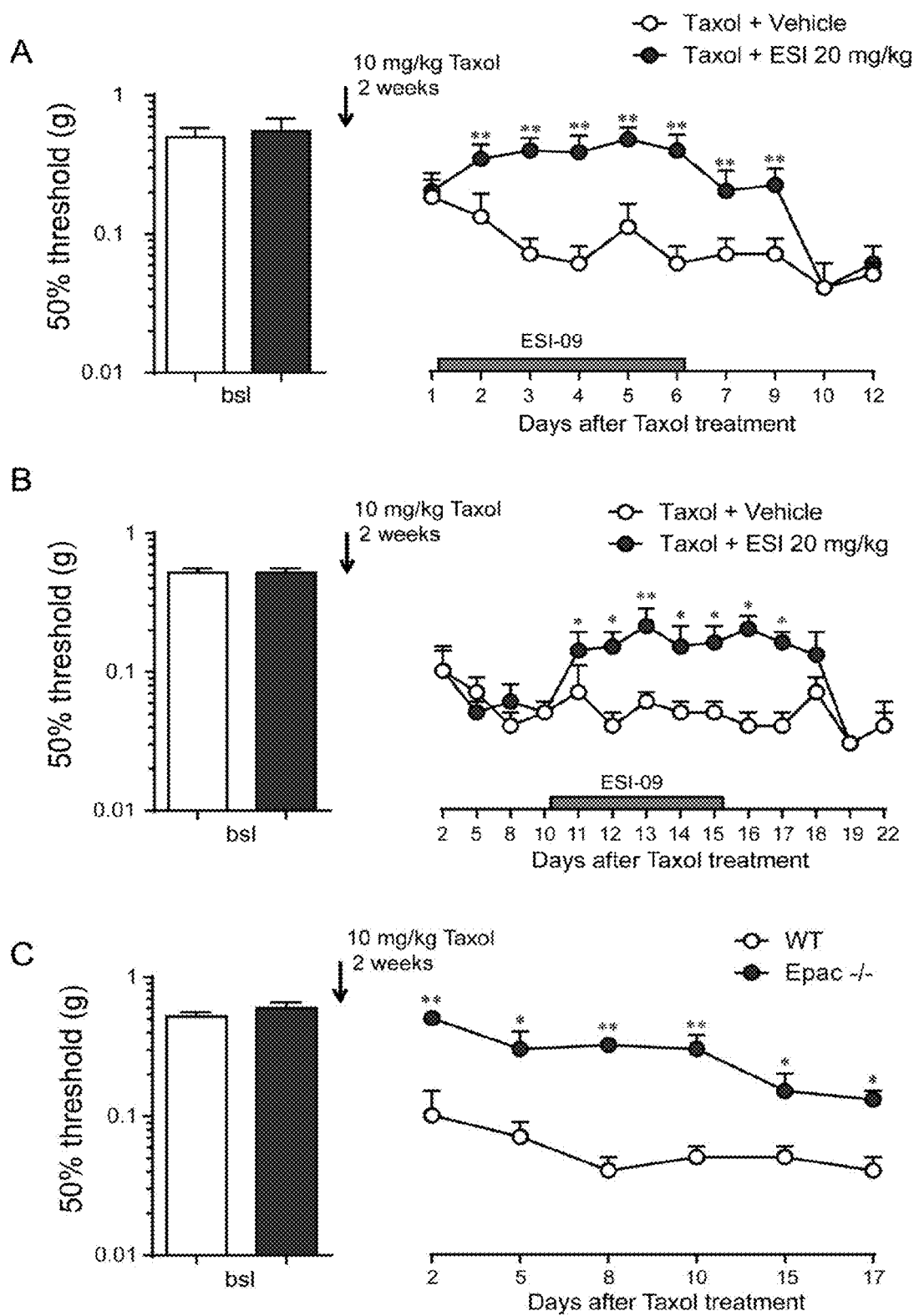
FIG. 4. Effect of ESI-09 on chemotherapy-induced mechanical allodynia. Mice (n=5/group) were treated with paclitaxel (10 mg/kg, Monday, Wednesday and Friday) for two weeks. ESI-09 (20 mg/kg) or vehicle was given by oral gavage for 6 days starting on the first day (A) or 10 days (B) after completion of paclitaxel treatment. The sensitivity to mechanical stimulation was determined in wild-type (n=5) and Epac1-/- (n=4) in the same paclitaxel model (C). Mechanical allodynia was monitored by von Frey hair using the up and down method. Data are expressed as means±SEM. *$p<0.05$, ** $p<0.01$.
Figure 5:
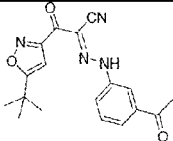
FIG. 5. Examples of compounds having a general formula of Formula I.
Figure 5:
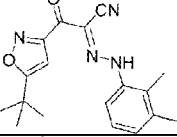
Figure 5:
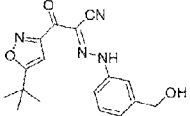
Figure 5:
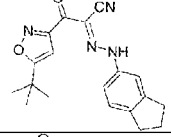
Figure 5:
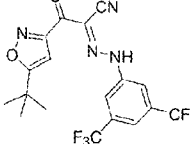
Figure 5:
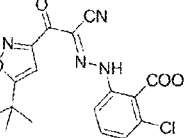
Figure 5:
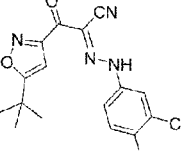
Figure 5:
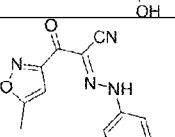
Figure 5:
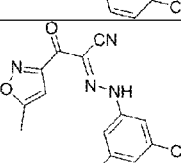

It has been shown that EPAC1−/− mice are protected against neuropathic pain in a model of nerve injury. The effect of ESI-09 in the spared nerve injury (SNI) model of chronic neuropathic pain was examined. ESI-09 (50 mg/kg) or vehicle was applied by oral gavage once every day for 6 days, starting 3 days after SNI surgery, when the mechanical allodynia was fully developed. As expected, mice treated with vehicle developed unilateral mechanical allodynia (FIG. 4A). Oral administration of ESI-09 almost completely reversed the mechanical allodynia that develops in the ipsilateral paw in response to SNI (FIG. 1A), without affecting the normal mechanical sensitivity in the contralateral paw (FIG. 4B). The beneficial effect of ESI-09 was maintained for 48 hours after the last dose.

Effect of ESI-09 on Chemotherapy-Induced Peripheral Neuropathy (CIPN) Model.

Chemotherapy-induced peripheral neuropathy is a frequent side effect of cancer treatment, and currently there are no FDA-approved drugs to treat or prevent chemotherapy-induced neuropathy. The model of paclitaxel-induced mechanical allodynia to investigate the potential effect of ESI-09 on chemotherapy-induced neuropathy. Mice were treated with three doses (10 mg/kg/dose) of paclitaxel per week for 2 weeks. Administration of ESI-09 was started on the first day after completion of paclitaxel treatment when there was clear allodynia present. Mice were treated daily with ESI-09 (20 mg/kg) or vehicle by oral gavage for 6 days. The data in FIG. 4A demonstrate that ESI-09 treatment almost completely rescued the mechanical allodynia that develops in response to paclitaxel treatment. The beneficial effect of treatment was detectable until 72 hours after the last dose of ESI-09. In a second set of experiments, ESI-09 treatment was delayed until 10 days after the completion of paclitaxel treatment. Also during this later phase of paclitaxel-induced neuropathy, ESI-09 significantly inhibited mechanical allodynia.

To determine whether the beneficial effect of ESI-09 on chemotherapy-induced mechanical allodynia was also mediated by Epac1, the effect of paclitaxel in Epac1−/− mice was examined. The paclitaxel-induced mechanical allodynia was markedly reduced in Epac1−/− mice as compared to WT controls. These findings indicate that Epac1 is required for development of mechanical allodynia in the chemotherapy model of chronic neuropathic pain and that treatment with the Epac inhibitor ESI-09 reverses already existing mechanical allodynia in this model.

The invention claimed is:

1. A method of treating pain comprising administering an effective amount of an EPAC inhibitor having a general formula of:

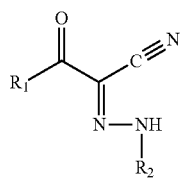

Formula I where $R_1$ and $R_2$ are independently substituted or unsubstituted cycloalkyl, substituted or unsubstituted heterocycle, substituted or unsubstituted aryl, or substituted or unsubstituted heteroaryl to a subject in need of such treatment.

2. The method of claim 1, wherein $R_1$ is a substituted isoxazole.

3. The method of claim 2, wherein the substituted isoxazole has linear alkyl, branched alkyl, or cycloalkyl substitution.

4. The method of claim 2, wherein the substituted isoxazole is methyl, ethyl, n-propyl, iso-propyl), n-butyl, sec-butyl, iso-butyl, tert-butyl, neo-pentyl, n-pentyl, or isopenyl substituted isoxazole.

5. The method of claim 2, wherein $R_1$ is a 5-methyl isoxazole or a 5-tert-butyl isoxazole.

6. The method of claim 1, wherein $R_2$ is a substituted or unsubstituted phenyl.

7. The method of claim 6, wherein $R_2$ is a substituted phenyl having one or more substituent selected from bromo, fluoro, chloro, iodo, or combinations thereof.

8. The method of claim 6, wherein $R_2$ is a 3-chlorophenyl; 2-chlorophenyl; 4-chlorophenyl; phenyl; 3,6-dichlorophenyl; 3-methylphenyl, 3-trifluoromethylphenyl; 3-nitrophenyl; 4-methylphenyl, 3,5-dichlorophenyl; 4-bromophenyl; 3-bromophenyl; 3,6-dimethylphenyl; benzopyridine; 2,3-dichlorophenyl; 3-ethynyl; benzoic acid ethyl ester; 3-benzonitrile; 3-acetylphenyl; 2,3-methylphenyl; 3-ethoxyphenyl; indane; 3,5-di-trifluoromethylphenyl; 6-chloro-benzoic acid; or 3-chloro, 4-hydroxyphenyl.

9. The method of claim 1, wherein the compound is selected from N-(5-tert-Butyl-isoxazol-3-yl)-2-[(3-chlorophenyl)-hydrazono]-2-cyanoacetamide (HJC0683); 2-[(3-Chlorophenyl)-hydrazono]-2-cyano-N-(5-methyl-isoxazol-3-yl)acetamide (HJC0692); 3-(5-tert-Butyl-isoxazol-3-yl)-2-[(2-chlorophenyl)-hydrazono]-3-oxo-propionitrile (HJC0693); 3-(5-tert-Butyl-isoxazol-3-yl)-2-[(4-chlorophenyl)-hydrazono]-3-oxo-propionitrile (HJC0694); 3-(5-tert-Butyl-isoxazol-3-yl)-3-oxo-2-(phenyl-hydrazono)-propionitrile (HJC0695); 3-(5-tert-Butyl-isoxazol-3-yl)-2-[(2,5-dichlorophenyl)-hydrazono]-3-oxo-propionitrile (HJC0696); 3-(5-tert-Butyl-isoxazol-3-yl)-3-oxo-2-(m-tolyl-hydrazono)propionitrile (HJC0712); 3-(5-tert-Butyl-isoxazol-3-yl)-3-oxo-2-[(3-trifluoromethyl-phenyl)-hydrazono]propionitrile (HJC0720); 3-(5-tert-Butyl-isoxazol-3-yl)-2-[(3-nitrophenyl)-hydrazono]-3-oxo-propionitrile (HJC0721); 3-(5-tert-Butyl-isoxazol-3-yl)-3-oxo-2-(p-tolyl-hydrazono)propionitrile (HJC0724); 3-(5-tert-Butyl-isoxazol-3-yl)-2-[(3,5-dichlorophenyl)-hydrazono]-3-oxo-propionitrile (HJC0726); 2-[(4-Bromophenyl)-hydrazono]-3-(5-tert-butyl-isoxazol-3-yl)-3-oxo-propionitrile (HJC0742); 2-[(3-Bromophenyl)-hydrazono]-3-(5-tert-butyl-isoxazol-3-yl)-3-oxo-propionitrile (HJC0743); 3-(5-tert-Butyl-isoxazol-3-yl)-2-[(2,5-dimethylphenyl)-hydrazono]-3-oxo-propionitrile (HJC0744); 3-(5-tert-Butyl-isoxazol-3-yl)-3-oxo-2-(quinolin-6-yl-hydrazono)propionitrile (HJC0745); 3-(5-tert-Butyl-isoxazol-3-yl)-2-[(2,3-dichlorophenyl)-hydrazono]-3-oxo-propionitrile (HJC0750); 3-(5-tert-Butyl-isoxazol-3-yl)-2-[(3-ethynyl-phenyl)-hydrazono]-3-oxo-propionitrile (HJC0751); 3-{N-[2-(5-tert-Butyl-isoxazol-3-yl)-1-cyano-2-oxo-ethylidene]-hydrazino}benzoic acid ethyl ester (HJC0752); 3-{N-[2-(5-tert-Butyl-isoxazol-3-yl)-1-cyano-2-oxo-ethylidene]-hydrazino}benzonitrile (HJC0753); 2-[(3-Acetyl-phenyl)-hydrazono]-3-(5-tert-butyl-isoxazol-3-yl)-3-oxo-propionitrile (HJC0754); 3-(5-tert-Butyl-isoxazol-3-yl)-2-[(2,3-dimethylphenyl)-hydrazono]-3-oxo-propionitrile (HJC0755); 3-(5-tert-Butyl-isoxazol-3- yl)-2-[(3-hydroxymethylphenyl)-hydrazono]-3-oxo-propionitrile (HJC0756); 3-(5-tert-Butyl-isoxazol-3-yl)-2-(indan-5-yl-hydrazono)-3-oxo-propionitrile (HJC0757); 2-[(3,5-Bis-trifluoromethyl-phenyl)-hydrazono]-3-(5-tert-butyl-isoxazol-3-yl)-3-oxo-propionitrile (HJC0758); 2-{N-[2-(5-tert-Butyl-isoxazol-3-yl)-1-cyano-2-oxo-ethylidene]-hydrazino}-6-chloro-benzoic acid (HJC0759); 3-(5-tert-Butyl-isoxazol-3-yl)-2-[(3-chloro-4-hydroxy-phenyl)-hydrazono]-3-oxo-propionitrile (HJC0760); 2-[(3-Chloro-phenyl)-hydrazono]-3-(5-methyl-isoxazol-3-yl)-3-oxo-propionitrile (HJC0768); or 2-[(3,5-Dichlorophenyl)-hydrazono]-3-(5-methyl-isoxazol-3-yl)-3-oxo-propionitrile (HJC0770).

10. The method of claim 1, wherein the EPAC inhibitor is 3-(5-tert-Butyl-isoxazol-3-yl)-2-[(3-chlorophenyl)-hydrazono]-3-oxo-propionitrile (HJC0680, ESI-09).

11. The method of claim 1, wherein the pain is chronic or neuropathic pain.

12. The method of claim 11, wherein the chronic pain is chemotherapy-associated chronic pain.

* * * * *